United States Patent
Beck et al.

(10) Patent No.: US 6,794,526 B2
(45) Date of Patent: Sep. 21, 2004

(54) PROCESS FOR THE PREPARATION OF MANGANESE COMPLEXES OF SALEN COMPOUNDS

(75) Inventors: Gerhard Beck, Rheinfelden (DE); Claus Korhummel, Grenzach-Wyhlen (DE); Hanspeter Baier, Grenzach-Wyhlen (DE); Frank Bachmann, Freiburg (DE); Cornelia Makowka, Laufenburg (DE); Reiner Linde, Oberwil (CH); Bernd Kirrmann, Rheinfelden (DE)

(73) Assignee: Ciba Specialty Chemicals Corporation, Tarrytown, NY (US)

(*) Notice: Subject to any disclaimer, the term of this patent is extended or adjusted under 35 U.S.C. 154(b) by 0 days.

(21) Appl. No.: 10/312,999
(22) PCT Filed: Jun. 26, 2001
(86) PCT No.: PCT/EP01/07265
§ 371 (c)(1),
(2), (4) Date: Jan. 2, 2003
(87) PCT Pub. No.: WO02/02571
PCT Pub. Date: Jan. 10, 2002

(65) Prior Publication Data
US 2003/0100763 A1 May 29, 2003

(30) Foreign Application Priority Data
Jul. 5, 2000 (EP) .......................................... 00810589

(51) Int. Cl.$^7$ .................................................. C07F 13/00
(52) U.S. Cl. ........................................................ 556/34
(58) Field of Search ........................................... 556/34

(56) References Cited

FOREIGN PATENT DOCUMENTS

| DE | 19843875 | 3/2000 |
|----|----------|--------|
| EP | 0902083  | 3/1999 |
| EP | 0955289  | 11/1999 |

OTHER PUBLICATIONS

J. Bonadies et al., Inorg. Chem., vol. 28, No. 11, (1989), pp. 2037–2044.

D. Bardwell et al., J. Chem. Soc., Dalton Trans., No. 18, (1995), pp. 3071–3080.

*Primary Examiner*—Porfirio Nazario-Gonzalez
(74) *Attorney, Agent, or Firm*—Kevin T. Mansfield

(57) ABSTRACT

A process for the preparation of manganese complexes of salen compounds which comprises carrying out the reaction of a salen compound with a manganese compound in DMF is described. In a preferred embodiment, the salen compound itself is synthesised likewise in DMF and reacted without intermediate isolation to form the manganese complex.

9 Claims, No Drawings

PROCESS FOR THE PREPARATION OF MANGANESE COMPLEXES OF SALEN COMPOUNDS

The present invention relates to a process for the preparation of manganese complexes of salen compounds, to the compounds prepared according to that process, and to the use thereof in washing and cleaning solutions.

Manganese complexes of salen compounds are known, for example, from EP-A-902 083 and EP-A-955 289. They are usually prepared from the appropriate salen ligands by reaction with a manganese salt in ethanolic solution in the presence of air as oxidizing agent. The ligands themselves are obtained, for example, by reacting the appropriate di- or tri-amines with the appropriate o-hydroxyaldehydes in methanolic or ethanolic solution and crystallising out the ligands. Since, however, on an industrial scale working in methanol or ethanol at elevated temperature in the presence of air necessitates complex safety measures, the need existed for an improved method of synthesis.

It has now been found, surprisingly, that the reaction of the ligand with the manganese salt can advantageously be carried out in dimethylformamide (DMF) as solvent, and at the same time it is possible to operate at a temperature sufficiently far below the flash point of the solvent that even in the presence of air there are no safety problems. The preparation of the ligand can be carried out, for example, in water or, preferably, likewise in DMF. Surprisingly, it is even possible to carry out the synthesis of the ligand and the preparation of the manganese complex in DMF as a "one-pot reaction", that is to say without isolation and purification of the ligand.

The present invention accordingly relates to a process for the preparation of manganese complexes of salen compounds of formula

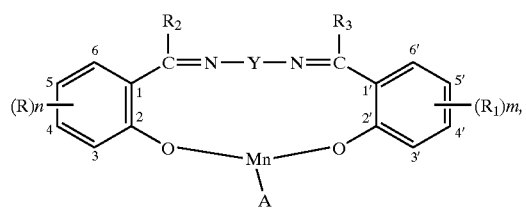

(1)

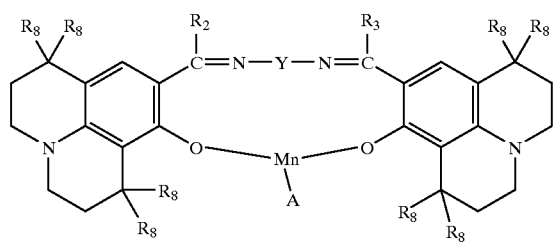

or (2)

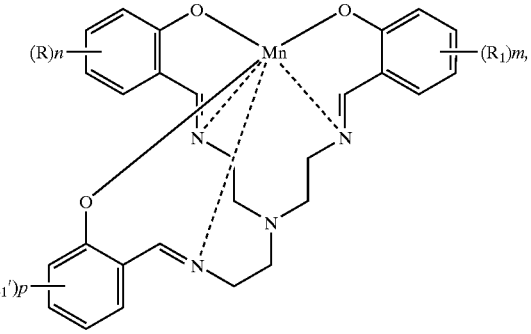

(3)

in which formulae

A is an anion;

n, m and p are each independently of the others 0, 1, 2 or 3,

R, $R_1$ and $R_1'$ are each independently of the others cyano; halogen; $OR_4$ or $COOR_4$, wherein $R_4$ is hydrogen or linear or branched $C_1$–$C_4$alkyl; nitro; linear or branched $C_1$–$C_8$alkyl; linear or branched partially fluorinated or perfluorinated $C_1$–$C_8$alkyl; $NR_5R_6$, wherein $R_5$ and $R_6$ are identical or different and are each independently of the other hydrogen or linear or branched $C_1$–$C_{12}$alkyl; or linear or branched $C_1$–$C_8$alkyl-$R_7$, wherein $R_7$ is a radical $NH_2$, $OR_4$, $COOR_4$ or $NR_5R_6$ as defined above; or —$CH_2$—$N^{\oplus}R_4R_6R_7$ or —$N^{\oplus}R_4R_5R_6$, wherein $R_4$, $R_5$ and $R_6$ are as defined above, $R_2$ and $R_3$ are each independently of the other hydrogen, linear or branched $C_1$–$C_4$alkyl or unsubstituted aryl or aryl that is substituted by cyano; by halogen; by $OR_4$ or $COOR_4$, wherein $R_4$ is hydrogen or linear or branched $C_1$–$C_4$alkyl; by nitro; by linear or branched $C_1$–$C_8$alkyl; by $NHR_5$ or $NR_5R_6$, wherein $R_5$ and $R_6$ are identical or different and are each hydrogen or linear or branched $C_1$–$C_{12}$alkyl or wherein $R_5$ and $R_6$ together with the nitrogen atom linking them form a 5-, 6- or 7-membered ring that may contain further hetero atoms; or by linear or branched $C_1$–$C_8$alkyl-$R_7$, wherein $R_7$ is a radical $NH_2$, $OR_4$, $COOR_4$ or $NR_5R_6$ as defined above; or by —$N^{\oplus}R_4R_5R_6$, wherein $R_4$, $R_5$ and $R_6$ are as defined above, $R_8$ radicals are each independently of the others hydrogen or linear or branched $C_1$–$C_4$alkyl, Y is a linear or branched alkylene radical of formula —$[C(R_4)_2]_r$—, wherein r is an integer from 1 to 8 and the $R_4$ radicals are each independently of any other(s) as defined above; —CX=CX—, wherein X is cyano, linear or branched $C_1$–$C_8$alkyl or di(linear or branched $C_1$–$C_8$alkyl)amino; —$(CH_2)_q$—$NR_4$—$(CH_2)_q$—, wherein $R_4$ is as defined above and q is 1, 2, 3 or 4; or a 1,2-cyclohexylene radical of formula:

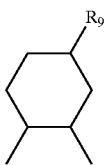 or a 1,2-aryl radical of formula 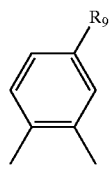

wherein $R_9$ is hydrogen, $SO_3H$, $CH_2OH$ or $CH_2NH_2$, wherein in formula (1) the phenyl rings may together carry no more than three tert-butyl substituents, and wherein, when Y is 2-hydroxypropylene and m and n are each 0, $R_2$ and $R_3$ may not both be H, and wherein when Y is ethylene or o-phenylene and m and n are each 0 and MnO is used as the manganese compound, $R_2$ and $R_3$ may not both be H, which process comprises reacting a ligand of formula (4)

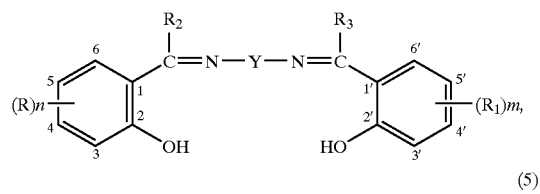

(5)

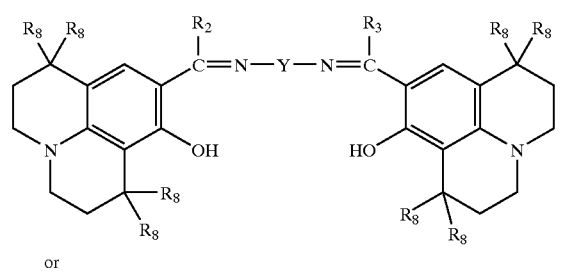

or (6)

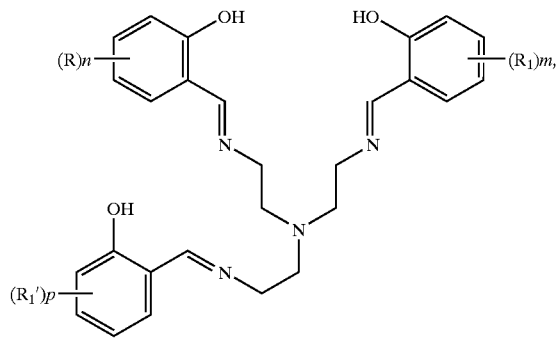

wherein R, $R_1$, $R_1'$, $R_2$, $R_3$, $R_4$, $R_5$, $R_6$, $R_7$, $R_8$, $R_9$, Y, A, n, m and p are as defined for formulae (1), (2) and (3), with a manganese compound in dimethylformamide as solvent.

In the compounds of formula (1) or (3) in which n, m or p is 2 or 3, the radicals R, $R_1$ and $R_1'$ have identical or different meanings. The same applies to compounds of formula (2) in respect of the $R_8$ radicals.

When Y is a 1,2-cyclohexylene radical, that radical may be in either of its stereoisomeric cis/trans forms.

Preferably, Y is a radical of formula —$(CH_2)_r$— wherein r is an integer from 1 to 8, or a radical of formula —$C(R_5)_2$—$(CH_2)_p$—$C(R_5)_2$— wherein p is a number from 0 to 6 and $R_5$ is hydrogen or $C_1$–$C_4$alkyl.

In especially preferred compounds of formulae (1) and (2), Y is a radical of formula —$(CH_2)_r$— wherein r is an integer from 1 to 4, or a radical of formula —$(CR_5)_2$—$(CR_5)_2$— wherein the $R_5$ radicals are each independently of the others hydrogen or methyl.

Halogen is preferably chlorine, bromine or fluorine, chlorine being especially preferred.

When R, $R_1$ or $R_1'$ is di($C_1$–$C_{12}$alkyl)amino, the alkyl group may be straight-chain or branched. Preferably it contains from 1 to 8, especially from 1 to 4, and more especially 1 or 2, carbon atoms.

Preferably, the radicals R, $R_1$ and $R_1'$ are hydrogen, nitro, $OR_4$, $COOR_4$ or $N(R_4)_2$, wherein $R_4$ is hydrogen or $C_1$–$C_4$alkyl, especially methyl or ethyl.

The radicals $R_2$ and $R_3$ are especially hydrogen, methyl, ethyl or unsubstituted phenyl.

Aryl is, for example, naphthyl or especially phenyl.

When $R_5$ and $R_6$ together with the nitrogen atom linking them is a 5-, 6- or 7-membered ring, that ring is especially a pyrrolidine, piperidine, morpholine or piperazine ring. The piperazine ring may be substituted, for example by alkyl, at the nitrogen atom that is not bonded to the phenyl radical.

Suitable anions include, for example, halide, for example chloride, perchlorate, sulfate, nitrate, hydroxide, $BF_4^-$, $PF_6^-$, carboxylate, acetate, tosylate and triflate. Of those, preference is given to chloride, acetate and carboxylate.

The ligands of formulae (4), (5) and (6) are known or can be prepared in a manner known per se.

In the process according to the invention, the reaction of those ligands with a manganese compound is carried out in DMF at a temperature of from approximately 10° C. to the boiling point of DMF, but preferably at a temperature of from 20 to 70° C., especially from 20 to 40° C.

The manganese compounds used are especially manganese(II) salts, especially manganese(II) chloride, sulfate or acetate.

Preferably, the manganese compound is added in slight excess, especially an excess of from 0.5 to 3%.

During the reaction, preferably air, as oxidizing agent, is passed through the reaction mixture, but it is also possible to use other oxidizing agents.

After the reaction, the manganese complex is isolated in a manner known per se, for example by crystallising it out by the addition of sodium chloride and then distilling off the DMF at elevated temperature in vacuo, suspending the residue in water and filtering.

In an especially preferred embodiment of the process according to the invention, the ligands used have not been formed and isolated beforehand but instead the synthesis of the ligand and the reaction to form the manganese complex are carried out in DMF as a so-called one-pot reaction.

The present invention accordingly relates also to a process for the preparation of manganese complexes of the above formulae (1), (2) and (3) which comprises, in DMF as solvent, reacting a diamine of formula

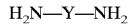 (7)

with an o-hydroxybenzaldehyde of formula (8)

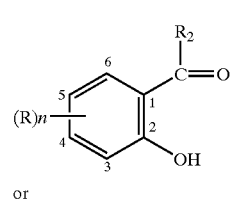

or

-continued

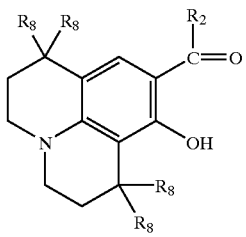

(9)

or reacting the compound of formula

N(—CH$_2$—CH$_2$—NH$_2$)$_3$ (10)

with an o-hydroxybenzaldehyde of formula (8), in which formulae R, R$_2$, R$_8$ and n are as defined for formulae (1) and (2), and then, without intermediate isolation, reacting the resulting salen compound with a manganese compound to form a manganese complex of formula (1), (2) or (3).

The first reaction is carried out at approximately from 10 to 40° C., preferably at room temperature, and di- or tri-amine and aldehyde are preferably used approximately in a molar ratio of 1:2 or 1:3, respectively.

The reaction conditions for the second step correspond to the conditions described above for the synthesis of the manganese complexes from ligand and manganese compound.

The manganese complexes are in that manner obtained with a good level of purity and a high yield according to a very simple process. They are used especially as catalysts that enhance the action of peroxy compounds in washing, cleaning and disinfecting procedures.

The following Examples serve to illustrate the invention but do not limit the invention thereto. Unless specified otherwise, parts and percentages relate to weight.

EXAMPLE 1

12 kg of 4,4'-[1,2-ethanediylbis(nitrilomethylidyne)]bis-1,3-benzenediol and 115 kg of N,N-dimethylformamide are introduced into a vessel. With vigorous stirring, 9.9 kg of manganese(II) acetate×4H$_2$O are introduced into the yellow suspension. Using a submerged tube, 10 litres of air per minute are passed through the reaction mixture, in the course of which the mixture is heated to 30° C., and that temperature is maintained for 2 hours. When the reaction is complete, 26 kg of sodium chloride are added, as a result of which the manganese complex crystallises out. The DMF is removed from the reaction mixture by distillation at 50 mbar at a temperature of from 65 to 77° C. 120 litres of water are added to the residue and the resulting brown suspension is cooled to room temperature. A further 2 kg of sodium chloride are then added and the reaction mixture is stirred for a further 30 minutes and then filtered. The residue is washed with 10% sodium chloride solution.

The filter cake is then dried for 24 hours at 100° C. in vacuo. 15 kg of product of formula

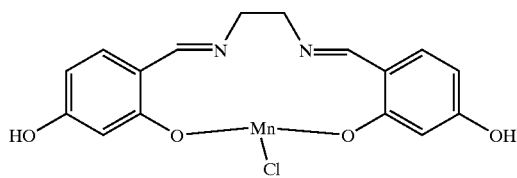

having a high level of purity are obtained.

EXAMPLE 2

69 g of 2,4-dihydroxybenzaldehyde are introduced into a 1 litre, double-walled ground-necked flask and 750 ml of DMF are added thereto. At room temperature, 15 g of ethylenediamine are then added in the course of 5 minutes and the mixture is subsequently stirred for approximately a further 15 minutes, the temperature rising to approximately 30° C. Using a gas inlet tube and a rotameter, 5 l/min of air are introduced and at 30° C. 61.8 g of manganese(II) acetate tetrahydrate are added. After 1 hour, 200 g of sodium chloride are added and stirring is carried out for a further 1 hour until ligand can no longer be detected by thin-layer chromatography.

The DMF is then distilled off from the reaction mixture at 60° C. and 30 mbar. The resulting brown residue is cooled to 50° C. and suspended in 750 ml of water. The resulting brown suspension is cooled to 20° C., stirred for a further 30 minutes and filtered. The filter cake is washed with 10% sodium chloride solution and then dried in vacuo at 75° C.

92.0 g of manganese complex of the formula given in Example 1 are obtained in a high level of purity.

What is claimed is:
1. A process for the preparation of a manganese complex of salen compounds of formula

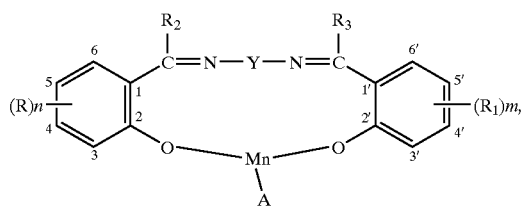

(1)

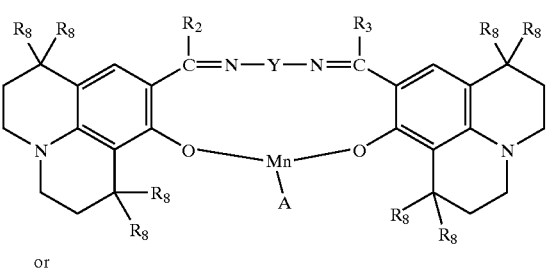

(2)

or

-continued

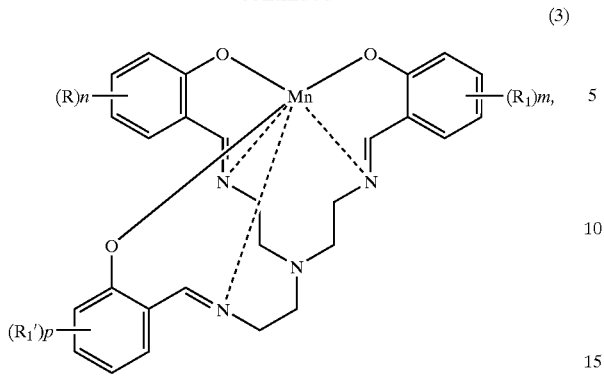
(3)

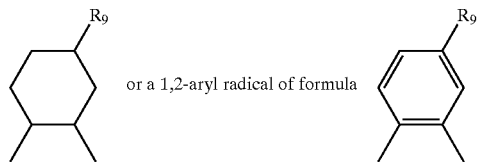
or a 1,2-aryl radical of formula wherein $R_9$ is hydrogen, $SO_3H$, $CH_2OH$ or $CH_2NH_2$, wherein in formula (1) the phenyl rings may together carry no more than three tert-butyl substituents, and wherein, when Y is 2-hydroxypropylene and m and n are each 0, $R_2$ and $R_3$ may not both be H, which comprises reacting a ligand of formula

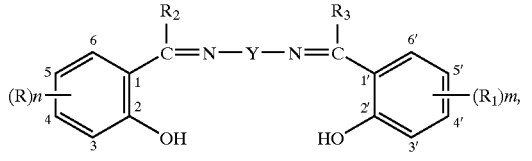
(4)

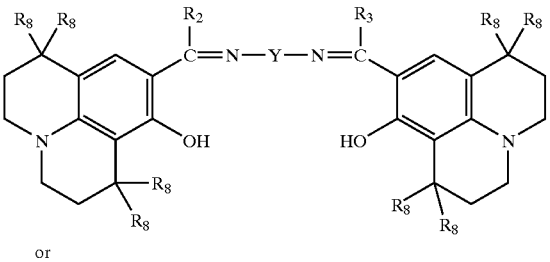
(5)

or

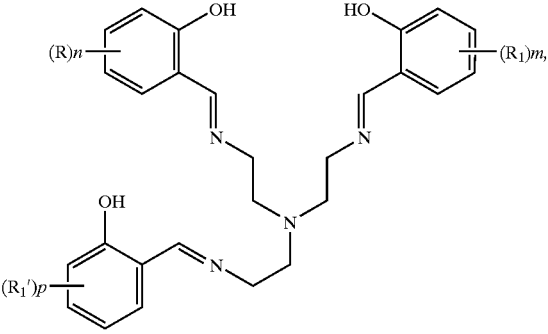
(6)

wherein R, $R_1$, $R_1'$, $R_2$, $R_3$, $R_4$, $R_5$, $R_6$, $R_7$, $R_8$, $R_9$, Y, A, n, m and p are as defined for formulae (1), (2) and (3), with a manganese(II) salt in dimethylformamide as solvent.

in which formulae

A is an anion;

n, m and p are each independently of the others 0, 1, 2 or 3,

R, $R_1$ and $R_1'$ are each independently of the others cyano; halogen; $OR_4$ or $COOR_4$, wherein $R_4$ is hydrogen or linear or branched $C_1$–$C_4$alkyl; nitro; linear or branched $C_1$–$C_8$alkyl; linear or branched partially fluorinated or pertfluorinated $C_1$–$C_8$alkyl; $NR_5R_6$, wherein $R_5$ and $R_6$ are identical or different and are each independently of the other hydrogen or linear or branched $C_1$–$C_{12}$alkyl; or linear or branched $C_1$–$C_8$alkyl-$R_7$, wherein $R_7$ is a radical $NH_2$, $OR_4$, $COOR_4$ or $NR_5R_6$ as defined above; or -$CH_2$—$N^{\oplus}R_4R_6R_7$ or —$N^{\oplus}R_4R_5R_8$, wherein $R_4$, $R_5$ and $R_6$ are as defined above, $R_2$ and $R_3$ are each independently of the other hydrogen, linear or branched $C_1$–$C_4$alkyl or unsubstituted aryl or aryl that is substituted by cyano; by halogen; by $OR_4$ or $COOR_4$, wherein $R_4$ is hydrogen or linear or branched $C_1$–$C_4$alkyl; by nitro; by linear or branched $C_1$–$C_8$alkyl; by $NHR_5$ or $NR_5R_6$, wherein $R_5$ and $R_6$ are identical or different and are each hydrogen or linear or branched $C_1$–$C_{12}$alkyl or wherein $R_5$ and $R_6$ together with the nitrogen atom linking them form a 5-, 6- or 7-membered ring that may contain further hetero atoms; or by linear or branched $C_1$–$C_8$alkyl-$R_7$, wherein $R_7$ is a radical $NH_2$, $OR_4$, $COOR_4$ or $NR_5R_6$ as defined above; or by —$N^{\oplus}R_4R_5R_6$, wherein $R_4$, $R_5$ and $R_6$ are as defined above, $R_8$ radicals are each independently of the others hydrogen or linear or branched $C_1$–$C_4$alkyl, Y is a linear or branched alkylene radical of formula —[$C(R_4)_2$]$_r$—, wherein r is an integer from 1 to 8 and the $R_4$ radicals are each independently of any other(s) as defined above; —CX=CX—, wherein X is cyano, linear or branched $C_1$–$C_8$alkyl or di(linear or branched $C_1$–$C_8$alkyl)amino;

—($CH_2$)$_q$—$NR_4$—($CH_2$)$_q$—, wherein $R_4$ is as defined above and q is 1, 2, 3 or 4; or a 1,2-cyclohexylene radical of formula:

2. A process according to claim 1, wherein the synthesis of the ligand and the reaction to form the manganese complex are carried out in dimethylformamide in a one-pot reaction.

3. A process according to claim 1, which comprises reacting, in dimethylformamide as solvent, a diamine of formula $$H_2N—Y—NH_2 \quad (7)$$

with an o-hydroxybenzaldehyde of formula

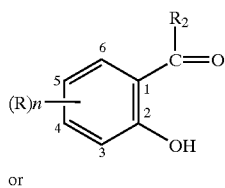
(8)

or

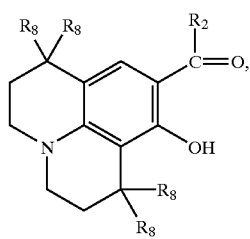
(9)

or reacting the compound of formula

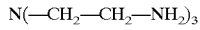
(10)

with an o-hydroxybenzaldehyde of formula (8), in which formulae Y, R, $R_2$, $R_9$ and n are as defined for formulae (1) and (2) in claim 1, and then, without intermediate isolation, reacting the resulting salen compound with a manganese(II) salt to form a manganese complex of formula (1), (2) or (3).

4. A process according to claim 1, wherein Y is a radical of formula $-(CH_2)_r-$ wherein r is an integer from 1 to 8, or a radical of formula $-C(R_5)_2-(CH_2)_p-C(R_5)_2-$ wherein p is a number from 0 to 6 and $R_5$ is hydrogen or $C_1-C_4$alkyl.

5. A process according to claim 1, wherein R, $R_1$ and $R_1'$ are hydrogen, nitro, $OR_4$, $COOR_4$ or $N(R_4)_2$, wherein $R_4$ is hydrogen or $C_1-C_4$alkyl.

6. A process according to claim 1, wherein $R_2$ and $R_3$ are hydrogen, methyl, ethyl or unsubstituted phenyl.

7. A process according to claim 1, which is carried out at a temperature of from approximately 20 to 70° C.

8. A process according to claim 1, wherein the manganese compound is added in an excess of from 0.5 to 3%.

9. A process according to claim 3, wherein the first reaction is carried out at approximately from 10 to 40° C., and the di- or tri-amine and aldehyde are used approximately in a molar ratio of 1:2 or 1:3.

* * * * *